US008858775B2

(12) United States Patent
Agg et al.

(10) Patent No.: US 8,858,775 B2
(45) Date of Patent: Oct. 14, 2014

(54) METHOD OF MANUFACTURING METAL WITH BIOCIDAL PROPERTIES

(75) Inventors: Philip James Agg, London (GB); James Timothy Shawcross, London (GB); Martin Edward Lee Pickford, London (GB); Andrew Derek Turner, Abingdon (GB); David Richard Lewis, London (GB)

(73) Assignee: Accentus Medical Limited, Didcott (GB)

( * ) Notice: Subject to any disclaimer, the term of this patent is extended or adjusted under 35 U.S.C. 154(b) by 0 days.

(21) Appl. No.: 12/680,757

(22) PCT Filed: Oct. 3, 2008

(86) PCT No.: PCT/GB2008/050894
§ 371 (c)(1),
(2), (4) Date: May 5, 2010

(87) PCT Pub. No.: WO2009/044203
PCT Pub. Date: Apr. 9, 2009

(65) Prior Publication Data
US 2010/0206733 A1    Aug. 19, 2010

(30) Foreign Application Priority Data

Oct. 3, 2007 (GB) .................................. 0719228.9
Mar. 4, 2008 (GB) .................................. 0804012.3
Mar. 31, 2008 (GB) .................................. 0805775.4

(51) Int. Cl.
C25D 11/26      (2006.01)
A61L 27/02      (2006.01)
(Continued)

(52) U.S. Cl.
CPC ....... *C25D 11/26* (2013.01); *A61F 2002/30927* (2013.01); *A61B 17/0642* (2013.01); *A61F 2/32* (2013.01); *A61F 2/3094* (2013.01);
(Continued)

(58) Field of Classification Search
USPC .................................. 205/200, 229, 322, 171
See application file for complete search history.

(56) References Cited

U.S. PATENT DOCUMENTS 3,634,204 A * 1/1972 Dhaka et al. .................. 438/287
4,027,393 A   6/1977 Ellis et al.
(Continued)

FOREIGN PATENT DOCUMENTS

AU    731730 B2    4/2001
AU    731732 B2    4/2001
(Continued)

OTHER PUBLICATIONS

Intellectual Property Office Search Report for Application No. GB0818043.2 dated May 22, 2009.
(Continued)

*Primary Examiner* — James Lin
*Assistant Examiner* — William Leader
(74) *Attorney, Agent, or Firm* — Tumey L.L.P.

(57) ABSTRACT

Metal objects are treated by anodising the metal object in contact with an acidic solution, and then subjecting the anodised metal object to a reversed voltage (compared to the anodising voltage). The thus-treated metal object is then contacted with a biocidal metal-containing solution. Biocidal metal is deposited on the surface of the metal object, resulting in improved biocidal properties.

14 Claims, 4 Drawing Sheets

(51) Int. Cl.
*A61L 27/54* (2006.01)
*A61L 27/50* (2006.01)
*A61F 2/30* (2006.01)
*A61B 17/064* (2006.01)
*A61F 2/32* (2006.01)
*A61F 2/28* (2006.01)
*A61B 17/68* (2006.01)

(52) U.S. Cl.
CPC ............... *A61F 2310/00616* (2013.01); *A61F 2002/30808* (2013.01); *A61L 2300/404* (2013.01); *A61F 2/30767* (2013.01); *A61L 27/02* (2013.01); *A61F 2310/00796* (2013.01); *A61L 2300/104* (2013.01); *A61L 27/54* (2013.01); *A61L 27/50* (2013.01); *A61F 2/28* (2013.01); *A61F 2310/00131* (2013.01); *A61F 2310/00407* (2013.01); *A61B 17/68* (2013.01); *A61F 2310/00598* (2013.01); *A61F 2310/00023* (2013.01); *A61F 2002/30733* (2013.01); *A61F 2310/00089* (2013.01); *A61F 2310/00095* (2013.01)
USPC ............ 205/171; 205/200; 205/229; 205/322

(56) References Cited

U.S. PATENT DOCUMENTS

| | | |
|---|---|---|
| 4,263,681 A | 4/1981 | Notton |
| 4,336,617 A | 6/1982 | Shikita et al. |
| 4,784,160 A | 11/1988 | Szilagyi |
| 4,806,218 A | 2/1989 | Hemminger et al. |
| 4,813,965 A | 3/1989 | Roberts |
| 4,818,572 A | 4/1989 | Shimamune et al. |
| 4,938,409 A | 7/1990 | Roberts |
| 5,032,129 A | 7/1991 | Kurze et al. |
| 5,132,003 A | 7/1992 | Mitani |
| 5,185,075 A | 2/1993 | Rosenberg et al. |
| 5,211,663 A | 5/1993 | Kovacs et al. |
| 5,211,832 A | 5/1993 | Cooper et al. |
| 5,310,464 A | 5/1994 | Redepenning |
| 5,454,886 A | 10/1995 | Burrell et al. |
| 5,468,562 A | 11/1995 | Farivar et al. |
| 5,478,237 A | 12/1995 | Ishizawa |
| 5,482,731 A | 1/1996 | Vargas-Gutierrez et al. |
| 5,492,763 A | 2/1996 | Barry et al. |
| 5,500,106 A * | 3/1996 | Goldberg ............ 205/166 |
| 5,503,704 A | 4/1996 | Bower et al. |
| 5,520,664 A | 5/1996 | Bricault, Jr. et al. |
| 5,595,638 A * | 1/1997 | Konuma et al. ......... 205/96 |
| 5,612,049 A | 3/1997 | Li et al. |
| 5,695,857 A | 12/1997 | Burrell et al. |
| 5,723,038 A | 3/1998 | Scharnweber et al. |
| 5,753,251 A | 5/1998 | Burrell et al. |
| 5,753,251 A | 5/1998 | Yamaguchi et al. |
| 5,770,255 A | 6/1998 | Burrell et al. |
| 5,833,463 A | 11/1998 | Hurson |
| 5,837,275 A | 11/1998 | Burrell et al. |
| 5,855,612 A | 1/1999 | Ohthuki et al. |
| 5,958,440 A | 9/1999 | Burrell et al. |
| 5,985,308 A | 11/1999 | Burrell et al. |
| 6,017,553 A | 1/2000 | Burrell et al. |
| 6,066,392 A | 5/2000 | Hisamoto et al. |
| 6,113,636 A | 9/2000 | Ogle |
| 6,180,162 B1 | 1/2001 | Shigeru et al. |
| 6,190,407 B1 | 2/2001 | Ogle et al. |
| 6,267,782 B1 * | 7/2001 | Ogle et al. ............ 623/1.1 |
| 6,322,588 B1 | 11/2001 | Ogle et al. |
| 6,346,186 B1 * | 2/2002 | Bjerrum et al. ......... 205/318 |
| 6,361,567 B1 | 3/2002 | Dearnaley |
| 6,365,220 B1 | 4/2002 | Burrell et al. |
| 6,482,444 B1 | 11/2002 | Bellantone et al. |
| 6,509,057 B2 | 1/2003 | Shigeru et al. |
| 6,544,288 B2 | 4/2003 | Osaka et al. |
| 6,582,715 B1 | 6/2003 | Barry et al. |
| 6,663,634 B2 | 12/2003 | Ahrens et al. |
| 6,689,170 B1 | 2/2004 | Larsson et al. |
| 6,719,987 B2 | 4/2004 | Burrell et al. |
| 6,866,859 B2 | 3/2005 | Trogolo et al. |
| 6,913,617 B1 | 7/2005 | Reiss |
| 7,029,566 B2 | 4/2006 | Yen |
| 7,048,541 B2 | 5/2006 | Hall et al. |
| 7,192,445 B2 | 3/2007 | Ellingsen et al. |
| 7,452,566 B2 | 11/2008 | Sul |
| 7,488,343 B2 | 2/2009 | O'Brien et al. |
| 2002/0099449 A1 | 7/2002 | Speitling |
| 2003/0045941 A1 | 3/2003 | Lewallen |
| 2004/0121290 A1 | 6/2004 | Minevski et al. |
| 2004/0161473 A1 | 8/2004 | Joshi |
| 2004/0234604 A1 | 11/2004 | Mecking et al. |
| 2004/0236338 A1 | 11/2004 | Hall |
| 2005/0177248 A1 | 8/2005 | Hall |
| 2005/0221259 A1 | 10/2005 | Anderson |
| 2006/0035039 A1 | 2/2006 | Ylitalo et al. |
| 2006/0198903 A1 | 9/2006 | Storey et al. |
| 2007/0187253 A1 | 8/2007 | Gilbert et al. |
| 2008/0011613 A1 | 1/2008 | Wang |
| 2009/0035722 A1 | 2/2009 | Balasundaram et al. |
| 2009/0093881 A1 | 4/2009 | Bandyopadhyay et al. |
| 2009/0104242 A1 | 4/2009 | Karlinsey |
| 2009/0124984 A1 | 5/2009 | Hanawa |
| 2009/0155335 A1 | 6/2009 | O'Shaughnessey et al. |
| 2009/0164027 A1 | 6/2009 | Zipprich |
| 2009/0198344 A1 | 8/2009 | Prentice et al. |
| 2009/0204213 A1 | 8/2009 | Liao et al. |

FOREIGN PATENT DOCUMENTS

| | | |
|---|---|---|
| BG | 62807 B1 | 8/2000 |
| CA | 2136456 C | 6/1999 |
| EP | 00257923 B1 | 1/1992 |
| EP | 0555004 A1 | 8/1993 |
| EP | 0761182 A3 | 3/1998 |
| EP | 00875146 B1 | 7/2002 |
| EP | 1207220 B1 | 1/2008 |
| GB | 2072514 A | 10/1981 |
| GB | 2073024 A | 10/1981 |
| GB | 2136448 A | 9/1984 |
| JP | 58-167798 A1 | 10/1983 |
| JP | 62-182298 A1 | 8/1987 |
| JP | 10-158889 A1 | 6/1998 |
| JP | 10-168597 A1 | 6/1998 |
| JP | 10-168598 A1 | 6/1998 |
| JP | 11-181596 A1 | 7/1999 |
| JP | 11-209895 A1 | 8/1999 |
| JP | 11-229186 A1 | 8/1999 |
| JP | 11-236699 A | 8/1999 |
| JP | 11-302570 A1 | 11/1999 |
| JP | 11-343592 A | 12/1999 |
| JP | 2005287985 A | 10/2005 |
| KR | 10-0910064 B1 | 7/2009 |
| RU | 2167526 C2 | 5/2001 |
| SI | 875146 T1 | 12/2002 |
| WO | WO 81/02667 A1 | 10/1981 |
| WO | WO 81/02668 A1 | 10/1981 |
| WO | WO 92/11043 A1 | 7/1992 |
| WO | WO 93/07924 A1 | 4/1993 |
| WO | WO 95/13704 A1 | 5/1995 |
| WO | WO 95/18637 A1 | 7/1995 |
| WO | WO 98/51231 A1 | 11/1998 |
| WO | WO 99/01089 A1 | 1/1999 |
| WO | WO 99/26666 A2 | 6/1999 |
| WO | WO 00/45724 A1 | 8/2000 |
| WO | WO 00/51659 A1 | 9/2000 |
| WO | WO 00/64505 A1 | 11/2000 |
| WO | WO 00/72777 A1 | 12/2000 |
| WO | WO 01/12246 A1 | 2/2001 |
| WO | WO 02/096475 A1 | 12/2002 |
| WO | WO 03/003938 A1 | 1/2003 |
| WO | WO 03/039609 A1 | 5/2003 |
| WO | WO 03/089023 A1 | 10/2003 |
| WO | WO03/094774 | 11/2003 |
| WO | WO 03/094774 A1 | 11/2003 |

(56) References Cited

FOREIGN PATENT DOCUMENTS

| WO | WO 2004/002543 A1 | 1/2004 |
| WO | WO2005/087982 | 9/2005 |
| WO | WO 2006/004686 A2 | 1/2006 |
| WO | WO 2006/058906 A1 | 6/2006 |
| WO | WO2006/104644 | 10/2006 |
| WO | WO 2006/104644 A2 | 10/2006 |
| WO | WO 2007/050327 A2 | 5/2007 |
| WO | WO 2007/144667 A2 | 12/2007 |
| WO | WO 2008/096160 A2 | 8/2008 |
| WO | WO 2009/044203 A1 | 4/2009 |
| WO | WO 2009/100792 A2 | 8/2009 |
| WO | WO 2009/100792 A3 | 8/2009 |

OTHER PUBLICATIONS

PCT International Search Report and Written Opinion for International Application No. PCT/GB2008/050894 dated Dec. 18, 2008.
Shirkhanzadeh et al., "Bioactive delivery systems for the slow release of antibiotics: incorporation of Ag+ ions into micro-porous hydroxyapatite coatings", Materials Letters 24, pp. 7-12, Jun. 1995.
Afshar, "Evaluation of electrical breakdown of anodic films on titanium in phosphate-base solutions" 2004.
Aladjem, "Review anodic oxidation of titanium and its alloys" 1973.
Aerospace Material Spec. (AMS 2487A), "Anodic treatment of titanium alloys solution pH 12.4 maximum" 1993-2006.
Aerospace Material Spec. (AMS 2488D), "Anodic treatment—titanium and titanium alloys solution pH 13 or higher" 1977-2006.
Chen, "Surface chemistry of TiCl4 on W(100)" 1996.
Chi, "Antibacterial activity of anodized aluminum with deposited silver" 2002.
Disegi, "Anodizing treatments for titanium implants" 1997.
Dunn, "Anodized layers on titanium and titanium alloy orthopedic materials for antimicrobial activity applications" 1992.
Dunn, "Formation and characterization of anodized layers on CP Ti and Ti-6Al-4OV" 1992.
Dunn, "Gentamicin sulfate attachment and release from anodized Ti-6Al-4V orthopedic materials" 2004.
Edwards, "Coating and surface treatment systems for metals" 1997.
Kawashita, "Bonelike apatite formation on anodically oxidized titanium metal in simulated body fluid" 2004.
Khadiri, "Characterization of titanium oxide thin films anodically grown in phosphoric acid" 2004.
Kokubo, "Novel bioactive materials with different mechanical properties" 2003.
Kurze et al., "Application fields of ANOF layers and composites" 1986.
Li et al., "Calcium phosphate formulation within sol-gel prepared titanium in vitro and in vivo" 1993.
Li et al., "The role of hydrated silica, titania and alumina in inducing apatite on implants" 1994.
Liu, "Surface modification of titanium, titanium alloys, and related materials for biomedical applications" 2004.
Marchenoir, "Study of porous layers formed by anodic oxidation of titanium under high voltage" (French) 1980.
Marchenoir, "Study of porous layers formed by anodic oxidation of titanium under high voltage" (English translation) 1980.
Martini, "Detachment of titanium & fluorhydroxypatite particles" 2003.
Necula, "In vitro antibacterial >activity of porous TiO2-Ag composite layers against methicillin-resistant *staphylococcus aureus*" 2009.
Olier, "Influence of the preparation conditions of titanium surfaces on the formation of anodic oxide layers" (French) 1980.
Olier, "Influence of the preparation conditions of titanium surfaces on the formation of anodic oxide layers" (English translation) 1980.
Schierholz, "Efficacy of silver-coated medical devices" 1998.
Schreckenbach, "Characterization of anodic spark-converted titanium surfaces for biomedical applications" 1999.
Shirkhanzadeh, "Nanoporous alkoxy-derived titanium oxide coating" 1998.
Souza, "EIS characterization of Ti anodic oxide porous films formed using modulated potential" 2007.
Suzuki et al., "Surface treatment of titanium (part 4) in vitro biocompatibility of titanium treated by the anodic spark oxidation" 1991.
Takasaki, "Elution of silver ions from A-type zeolite supporting silver ions in aqueous solutions" (Japanese) 1996.
Takasaki, "Elution of silver ions from A-type zeolite supporting silver ions in aqueous solutions" (English translation) 1996.
Tsukada, "Low-temperature electrochemical systhesis of ZrO2 films on zirconium substrates" 1997.
Xie, "Improvement of surface bioactivity on titanium by water and hydrogen plasma immersion ion implantation" 2005.
Yang, "Preparation of bioactive titanium metal via anodic oxidation treatment" 2004.
Yoshinari, "Influence of surface modifications to titanium on antibacterial activity in vitro" 2001.
Yu, "Synthesis and characterization of phoshated meso porous titanium dioxide with photocatalytic activity" 2003.
Yue, "Bioactive titanium metal surfaces with antimicrobial properties prepared by anodic oxidation treatment" 2009.

* cited by examiner

METHOD OF MANUFACTURING METAL WITH BIOCIDAL PROPERTIES

The present invention relates to a method of treatment of a metal to provide it with biocidal properties. In particular but not exclusively, the invention relates to treated metals that can be used to reduce irritation or infection in the body, when the body comes into contact with metal or metal objects placed on or in the body.

Metal materials come into contact with the body in numerous situations, for example in surgery, where implants are used, these implants being inserted into the tissue of the body, be this soft or hard tissue. In the case of cancer treatment of the bone for example, cancerous bone tissue is removed, and a prosthetic metal implant is used to replace that part of the bone that has been removed. Implants are also used for partial or full replacement of bones in joints (e.g. hips) and also in other fields such as dentistry and maxillofacial surgery. Implants for the foregoing (and other) uses may be of titanium metal or titanium alloy. Titanium metal and titanium alloy are biocompatible, and relatively strong and relatively light.

Further, metal comes into contact with the body in the jewellery industry. Much jewellery is made from metal alloys which are cheaper than using pure metals such as gold. However, in the case of jewellery, metal alloys have the disadvantage that they contain impurities, which may react with moisture in perspiration. Also, pitting of the metal alloy can occur due to the presence of chloride ions in the perspiration and this can cause a seat for bacteria to accumulate which can then result in skin infections if the metal alloy comes into contact with broken skin. Irritation and infection can occur not only for jewellery that pierces the body but also for jewellery that sits next to the skin if the wearer has sensitive skin.

As can be seen, in both the medical and jewellery fields, the use of metal which comes into contact with body tissue runs the risk of introducing infection, or infection occurring. In both areas it has been suggested that metallic silver might be electroplated onto metal. Silver is known to have biocidal properties and the silver controls infection without causing toxic effects to the subject. However such coatings may be undercut due to corrosion from body fluids and/or passivation of the implant surface, so that the coating may detach from the metal, which may lead to increased wear and cause tissue damage from detached particles containing silver.

The present invention seeks to overcome the problems associated with the prior art by providing an anodised metal material having both hardwearing and biocidal properties, which can reduce the risk of infection. The invention can also be used in the prevention of biofilm formation. The invention has applications in a number of areas of technology, including the medical fields, the jewellery industry and in other areas where a metal may come into contact with the body, for example when an individual is using a pen, handling cutlery or other domestic or industrial articles, or wearing spectacles, and this can have further applications to the healthcare industry where the risk of infection needs to be minimized. In effect the invention has applications in all areas where a metal article having been anodised according to a method of the invention, comes into contact with the skin, or body tissue; and in particular the invention is applicable to metal articles formed of metals such as titanium, or their alloys.

According to a first aspect of the invention, there is provided a method treating a metal object so as to form thereon a surface layer which is integral with the metal object, and which includes a biocidal material, the method comprising: (a) immersing the metal object, which is to provide a substrate for the surface layer, in an anodising electrolyte containing a solvent, and passivating the metal to form an anodised integral surface layer on the metal object; (b) continuing the application of a potential to produce pits through the integral surface and into the substrate;

(c) producing a hydrous metal oxide by (i) either applying a negative voltage to the metal object that has been anodised during steps (a and b), while in contact with the anodising electrolyte or (ii) contacting the metal object that has been anodized during steps (a and b) and with an electrolyte solution containing a reducible soluble salt of titanium or the substrate metal and applying a negative voltage or (iii) contacting the metal object with a chemical reducing agent after steps (a and b); and (d) removing or separating the anodised metal object resulting from step (c) from the anodising electrolyte, the electrolyte solution or chemical reducing agent, and contacting the anodised metal object with a solution containing a biocidal material so as to incorporate said biocidal material into the surface layer.

It is envisaged that in step (c) that a phosphate may be produced in addition to or as an alternative to a hydrous metal oxide.

It is preferred that there is a rinsing of the implant to remove anodizing electrolyte before contacting with a solution containing a biocidal material.

After anodization in steps (a) and (b), it is envisaged that the solution contained within the surface pits may contain a peroxy cationic complex of the substrate metal, which can be reduced electrochemically in step (c) (i) to a hydrous metal oxide of limited solubility. It is also envisaged that the electrolyte solution in step (c) (ii) may contain a peroxy cationic complex, preferably a peroxytitanyl, which can be reduced electrochemically within the pits to hydrous titania. Following the anodization of an object comprising for example Titanium, removal of the metal object from the anodizing solution, materials such as peroxytitanyl will be carried in the pit in the surface of the metal object and into the reducing solution where it will be reduced to hydrous titania in step (c) (iii).

In the case of chemical reduction, where again a hydrous metal oxide is produced, the chemical reducing agent may be selected from one or more of the following sodium sulphite, ferrous salts (chloride or sulphate), sodium nitrite, stannous chlorides or sulphates, chromous chlorides or sulphates, vanadous sulphates, hydrazine, borohydrides, or even acetone or formaldehyde under suitable conditions.

The use of the electrolyte solution with an added chemical reducing agent, like the voltage reversal, results in hydrous metal oxides being produced and these oxides have a high surface area. The high surface area allows for increased ion exchange with materials such as silver, which can be used as biocidal materials.

Preferably, in step (b) the metal object is anodised until pits are formed through said surface layer into the substrate metal and in step (d) the biocidal material is incorporated in said pits. There is a two stage process with step (a) comprising the initial process of passivation i.e. preparing the surface for pitting by growing a surface film and then (b) pitting itself.

The maximum voltage applied during anodization can define the thickness of the passive oxide film. Lower voltages applied subsequently may not affect the film thickness.

The voltage during passivation may be applied as a voltage increasing linearly with time to a limiting value or alternatively stepped voltages up to the maximum limit, or down to a lower subsequent value may be applied. It is also envisaged that multiple passivations may be used, where a voltage is applied repeatedly to prepare the metal surface for pitting.

These different types of applying voltage all come within the definition of applying a voltage.

Before moving on to step (d) there is rinsing of the anodised metal to remove residual electrolyte and then there is a subsequent contact with the solution containing the biocidal metals ions to maximise the incorporation of the biocidal metal ions in the surface layer on the metal object. The rinsing may be by using water or any appropriate solvent.

During the anodising procedure of step (a and b), a positive voltage is applied to the metal. During step (c) of process (i) or (ii), a voltage is applied to the metal in the opposite sense i.e is reversed, this being the negative voltage referred to herein in relation to step (c). It is preferred that the voltage reversal occurs after the end of step (b) that was used to create the pits. By pits, we mean wells or reservoirs that are able to store the biocidal material. As a result of the anodising and subsequent steps, the metal object has a hard outer surface formed of an anodised layer, grown out from the surface, (which can typically adsorb ~0.3-1.0 µg/cm$^2$ Ag) and dispersed within the surface of this layer are pits that can receive additional ions of the biocidal material such as silver ions. The matrix contained within the pits receiving the biocidal material may be relatively soft and porous relative to the anodized surface, thus combining the optimal properties of higher silver storage capacity with the material forming the harder anodized surface.

The biocidal material may comprise a biocidal metal and in particular, the biocidal metal is silver. It is envisaged that a colloidal type biocidal material may be used for example a protein colloid adsorbed on the hydrous titania surface that could also release nutrients into a site in the body, which may assist in healing of the body where the implant is positioned.

The positive voltage in step (a) may be 15-200 V (volts) but typically is in the range of 30 V to 150 V or even up to 750 V or 2000 V in an electrolyte with a high breakdown potential, such as lithium borate. Voltages that have been considered as useful are for example, 35 V or 100 V and these are particularly useful in the field of implants. After the growth of the passive layer (step a) of desired thickness, hardness and colour, pits may be grown in the surface in a different electrolyte, possibly at a lower potential—for example 2.1 M HPO$_4$ at 100 V as a separate step, followed by the electroreduction step to form hydrous titania in-situ.

The magnitude of the negative voltage may be maintained or regulated so as to be insufficient to cause electrolysis of the solvent. The magnitude of the negative voltage affects the absorptive capacity of the surface through the passage of a reductive current for a given period of time such that the charge passed is directly related to the creation of an adsorber matrix and hence the amount of biocidal material (e.g. metal, such as silver) which is subsequently incorporated into the surface of the metal object. If the magnitude of the negative voltage is too low over a given time period, the amount of biocidal metal subsequently incorporated may be insufficient to provide a desired level of biocidal properties but the process can be allowed to go on for a longer period to overcome this. The balance is providing a negative voltage that produces the level of biocidal material required to produce a biocidal/bacteriostatic effect and which includes the material within a time frame that is commercially viable. It is possible to determine the magnitudes of negative voltage which do not cause electrolysis of the electrolyte while enabling desired amounts of biocidal metal to be subsequently incorporated into the surface of the metal object by monitoring the reduction current.

The negative voltage may be applied at least until the current through the metal object has caused the passage of the sufficient charge to generate the desired adsorption capacity. Typically, this current will have fallen to less than 80% of its initial value, more typically to 60% or less of its initial value. However, values for the current of down to 20% may apply if the process is allowed to carry on for a longer period of time, for example up to 2 minutes.

Preferably, the biocidal material (e.g. metal, such as silver) is provided in the solution in the form of ions. The biocidal metal may be or may comprise silver, although other metals may be used in addition to or as alternatives to silver.

The metal of the metal object may comprise titanium or may comprise niobium, tantalum or zirconium, or an alloy comprising such a metal.

The anodising may be performed employing a liquid electrolyte preferably comprising phosphoric acid that has been dissolved in a diluent to make a more dilute solution to control the solution pH to within the desired range. The electrolyte may comprise water as solvent. Other electrolytes such as sulphuric acid, phosphate salt solutions or acetic acid may be used. Alkaline electrolytes such as sodium hydroxide may be used also. It is preferred that these electrolytes are in a diluted form for example 2.1 M H$_3$PO$_4$, 0.1 M H$_2$SO$_4$.

Preferably, movement or circulation of the electrolyte during anodising relative to the surface of the metal object during the anodising step is suppressed or inhibited to the extent possible in practice, at least during the period when microscopic pits are being formed through the said surface layer (b), although gentle agitation is desirable during the passivation phase (a) when high currents flow—thus minimising the generation of local heating effects. This is beneficial in improving process uniformity over both a single item, but also between an assembly of units being treated simultaneously. For example, during the pit growth period (b), it is preferred that no stirring of the electrolyte should be performed, and/or means (such as baffles or additives, such as gelling agents, to increase the viscosity of the electrolyte) to prevent or reduce electrolyte movement may be employed. It has been found that increased levels of hydrous metal oxide (e.g. hydrous titanium oxide) are formed when the electrolyte is not moved or circulated relative to the surface of the metal object during the part of the anodising step (b) when microscopic pits are being formed through the anodised surface layer into the substrate metal. It has also been found that higher levels of biocidal metal can be incorporated into sites on the thus anodised surface without giving rise to toxic effects when the resulting metal object is used.

The phosphoric acid may have a concentration in a range of from 0.01 M to 5.0 M, typically from 0.1 M to 3.0 M and in particular 2.0 M. An example of the concentration used in the medical field is 0.05 to 5.0 M, e.g. from 1.0 to 3.0 M and in the jewellery industry from 0.01 M to 5.0 M. Preferably, the pH of the acidic electrolyte should be maintained within the range of 0.5<pH<2.0—more ideally within the range 0.75<pH<1.75.

If an alkaline electrolyte is used the pH is greater than 7 and preferably is greater than 9 and more typically the pH is in the range of 10-14. The alkaline electrolyte can be a phosphate salt such as Na$_3$PO$_4$.

For example, in the case of a medical implant comprising titanium, when the molarity of the phosphoric acid is 2.0 M, the negative voltage may have a magnitude in a range of from −0.2 to −0.7 V with respect to an Ag/AgCl standard reference electrode. This voltage range with respect to an Ag/AgCl standard reference electrode would be selected to avoid electrolysis of the water solvent at less than −0.7V. A less negative voltage (e.g. −0.1 V) has the effect that less silver loading can be attained in the finished metal, reducing its biocidal properties, due to the passage of a smaller reduction current.

In instances where other metal substrates or anodising electrolytes are used instead of phosphoric acid, sulphuric acid or acetic acid the magnitude of the negative (i.e. reverse) voltage may need to be adjusted to provide the desired effects due to factors such as changes in pH, or even temperature.

The anodised metal object may be treated (e.g. rinsed) with a solvent (e.g. water) to remove electrolyte and soluble cations prior to performing the said ion exchange.

The geometric surface area of the metal object can be determined by conventional means such as the use of standard measuring devices such as Computer Aided Design (CAD), callipers, micrometers and rulers combined with a geometric model of the item being treated, or more advanced optical methods such as laser scanning. This measurement does not however take into account microscopic surface features or surface roughness of the metal. This microscopic surface area is an important factor in determining and controlling how much charge is passed during the anodisation step e.g. coulomb/cm$^2$. The microscopic surface area can be determined, for example, by immersion of the metal object (such as an orthopaedic implant) in an electrolyte, and measuring the double layer capacitance and comparing this to calibrated standards under identical conditions of temperature and electrolyte concentration. The charge or current per microscopic surface area e.g. coulomb/cm$^2$ or mA/cm$^2$ is therefore typically used in the control of the anodising process. The ratio of microscopic to geometric area is known as the surface roughness factor and can be used to convert one area to the other. For example, a 10 μg/cm$^2$ silver loading on a geometric area basis would correspond to a 5 μg/cm$^2$ silver loading on a microscopic areas basis for a roughness factor of 2. The silver loading per geometric area e.g. μg/cm$^2$ is typically used for an orthopaedic implant.

The anodising may be performed with a maximum current density in a range of from 0.1 to 100 mA/cm$^2$, preferably 0.1 to 50 mA/cm$^2$, or more typically 1 to 10 mA/cm$^2$, e.g. 5 mA/cm$^2$ or thereabouts. This determines the time taken for passivation—i.e. the raising of the applied potential from 0 to the maximum value (e.g. of 100V), when the current falls to a significantly lower value. Alternatively, an applied voltage linearly increasing with time or as voltage steps may be applied to control the passivation period, this in turn will have an influence on the subsequent pit growth phase (b). As an overview, typically, the initial value of the passive current density used in the pit-growth part of the process is typically in the range of 0.05-0.5 mA/cm$^2$ and the value for the current density at the end of this phase is typically in the range 0.2-2.0 mA/cm$^2$ The amount of charge employed for anodising (steps a and b) may be in a range of from 1 to 10 coulombs/cm$^2$, e.g. from 2 to 5 coulomb/cm$^2$. The anodising current may be passed during a period of from 0.5 to 8 hours, more particularly 1 to 6 hours, e.g. from 2 to 4 hours.

The negative voltage may be applied to the metal object at least until the current through the metal object falls to a lower value relative to the initial reduction current on its application, e.g. preferably no more than 20% of its initial value (e.g. converging on zero or substantially zero). As an overview, typically, the initial value of the reduction current density used in the process is in the range of 0.05-2.0 mA/cm$^2$ and the value for the current density at the end of the reduction voltage phase is 0.01-0.4 mA/cm$^2$. The time over which the negative voltage is applied until the current falls to a suitably low value may be less than 300 s, and may usually be less than 120 s.

The present invention also provides methods of treating a metal object as specified in one or more of the claims following this description.

According to a further aspect of the invention, there is provided a metal object obtained by the methods described above and hereinafter.

The metal object may be in the form of an implant, a medical implement or device or jewellery. In particular, in the case of a medical implement or device, this could include any type of device or tool that comes into contact with the body, for example pace-makers, stents, skin staples, scalpels, trocars, pins for bones or even medical implements such as scalpels or tissue clamps which are used during surgery.

The metal object has desirable biocidal properties to suppress and/or control infection without toxic effects on an individual, whether animal or human, that comes into contact with the material.

Implants according to the invention can be used for many medical and surgical purposes, including full and partial hip replacements, implants useful in maxillofacial, trauma, orthodontal and orthopaedic applications, arthroscopic devices, dental implants, neurological apparatus and parts (such as staples, nails and pins) used in cardiovascular and general surgery.

The jewellery that can be made from the metal object according to the invention can include all types of jewellery. The jewellery can be conventional jewellery such as rings, necklaces and bracelets or the jewellery can be of the type that is held within an aperture in the body, for example jewellery that is applied to the body transcutaneously, i.e. the jewellery pierces the body e.g. earrings, navel rings, rings to be inserted through other fleshy parts of the body such as the lips, cheeks etc.

The metals that may be used to make the implants or jewellery according to the invention may be titanium or a titanium alloy. One standard alloy for this purpose is titanium 90% with 6% aluminium and 4% vanadium (British Standard 7252). Alternatively the metal may comprise niobium, tantalum or zirconium, or alloys of these metals.

For an implant or jewellery for piercing the body, it may be desirable that the surface of the material is highly polished before production of the surface layer by anodising. In the case of implants, a highly polished surface reduces any tendency for local calcification when the implant comes into contact with the bone. A polished surface also permits smooth movement of muscle and tissue over the surface with minimal fretting or wear. Suitable polishing may be attained by known techniques, such as (e.g.) mechanical polishing and/or electropolishing.

The metal object can initially be polished to provide a very smooth surface. Titanium alloy can be electro-polished using acetic acid, or a mixture of nitric and hydrofluoric acids. Alternatively the material might be subjected to a combination of anodic passivation with mechanical polishing, which may be referred to as electrolinishing, this process removing the oxide that protects surface roughness, the surface at that point then being electrochemically re-passivated, so producing a mirror-smooth finish. Various electrolytes are suitable for this purpose, including nitric acid mixed with sulphuric acid, sodium hydroxide, sodium phosphate, acetic acid or sodium hydroxide mixed with sodium nitrate. Techniques such as grit blasting or shot blasting or shot peening may also be used to prepare the surface (e.g. for subsequent application of hydroxyapatite by plasma spraying after biocidal ion loading, to stimulate localised bone attachment). Also, the surface may be spray coated with titanium to provide a rough surface.

After polishing or other treatment of the surface of the metal object, surface modification or conversion can take place. A layer of a hydrated metal oxide material which may include some phosphate is formed by anodising in a suitable electrolyte, so that the resulting layer builds out from the surface of the metal. Biocidal metal species, e.g. ions, can then be absorbed or adsorbed into the oxide and/or phosphate matrix in a subsequent step by treating the anodised metal surface with an aqueous salt solution. The biocidal metal species may be in the form of ions, for example silver ions (or $Cu^{++}$), and these ions can then be absorbed/adsorbed by ion exchange into the oxide and/or phosphate matrix, or a mixture thereof. Cations of palladium, platinum or even ruthenium could be absorbed in a similar way. If desired, deposited silver, platinum or palladium ions could then be converted to metal, or deposited ruthenium ions converted to insoluble $RuO_2$, within the oxide or phosphate surface coating, this reaction being performed chemically or electrochemically or by light.

The invention is further described with reference to the accompanying figures and with reference to an embodiment of the invention which is given by way of a non-limitative example only.

FIG. 1: shows a diagrammatic representation of the voltages and currents used during surface coating according to an embodiment of the invention;

Figure 1:
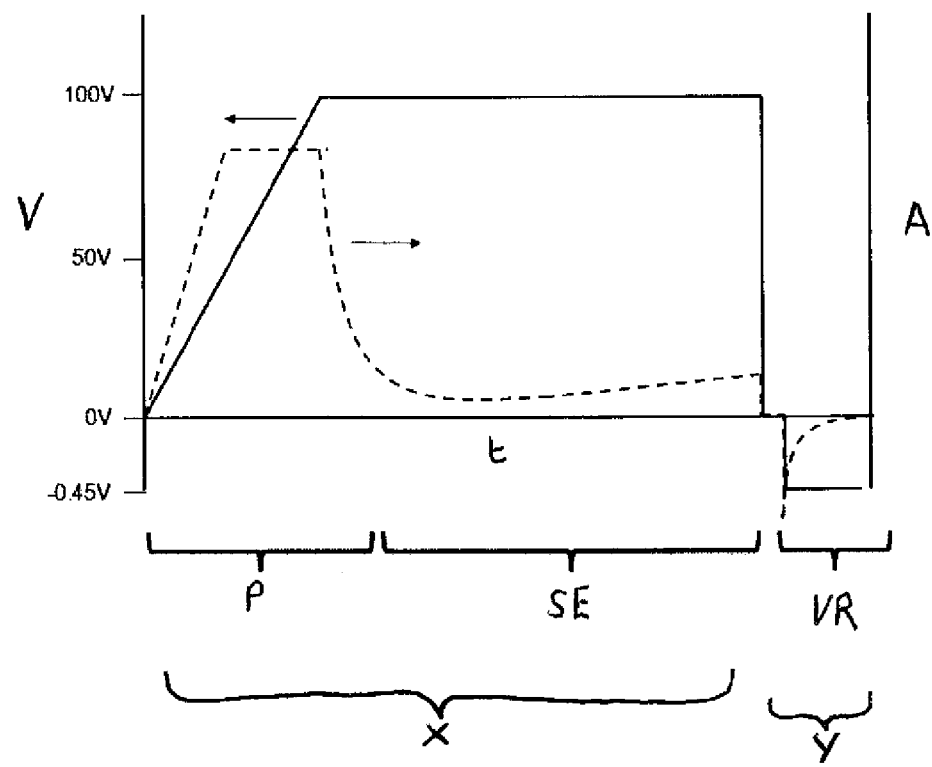

FIG. 1 illustrates typical current and voltage levels used in the anodizing of a titanium metal object. The voltage is shown as an unbroken line and the current as a broken line. The graph shows current (Amps) and voltage (V) applied over time (t). The voltage (not shown in scale) is increased, for example to 100V and at this stage passivation (shown as P) of the surface of the metal occurs, which results in a material that is integral with the titanium metal substrate. During the initial application of voltage the potential is normally controlled using a current limiter which could be in the range of 2.5-10 $mA/cm^2$ but higher levels can be used. During the current limited period the applied potential supplied from the power supply gradually increases as the thickness of the oxide film grows. The voltage is increased to a predetermined limit, which is selected according to the properties required for the surface material of the metal. When the voltage limit is reached, for example to 100 V, the current falls back to a low level, for example less than 1 $mA/cm^2$ and this drop in current level indicates that passivation has occurred. Once passivation occurs, the voltage is maintained to allow for surface engineering of the passivated metal surface (shown as SE) and pits are formed in the surface. The voltage level and the time selected for applying the voltage can be chosen according to the coverage and dimensions of the pits required for the surface. This passivation and surface engineering of the metal surface is shown as step (x). Once the passivation and the production of pits to a required format is complete, the metal object is subjected to a voltage reversal (shown as VR) which results in an observed negative current. The application of this negative voltage occurs at step (y) as shown. The voltage selected and the length of time the voltage is applied can alter the loading of the metal surface with ionic material that can produce a biocidal effect.

Figure 2:
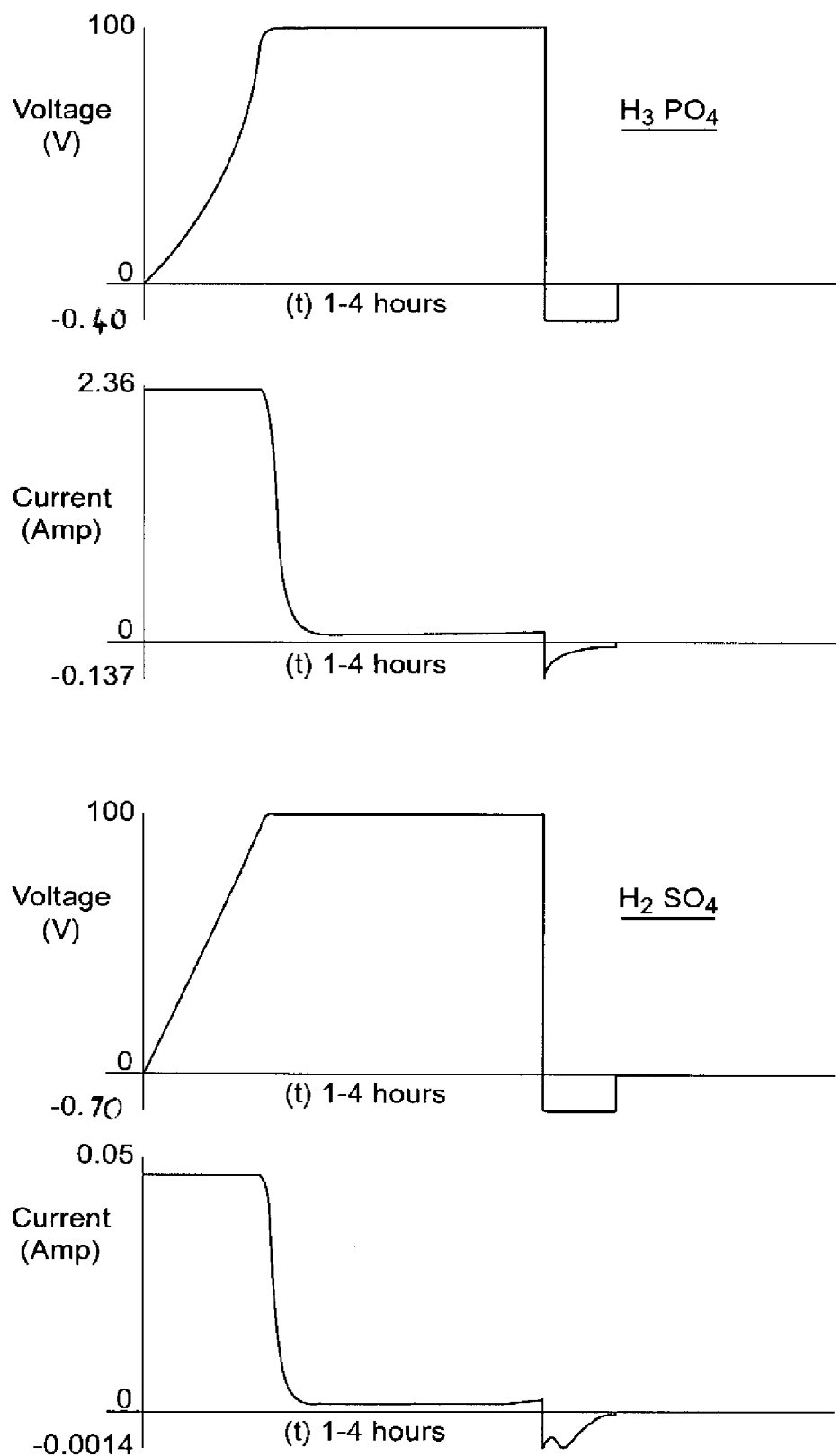
FIG. 2 shows the use of current reversal using different types of acids during the passivation process.

FIG. 2 shows traces of the changes in voltage and current levels over time when using a sulphuric (0.1 M) or phosphoric acid (2.1 M) electrolyte solution in which the metal material is placed for anodization. As can be seen, the trace produced over time for each process follows a similar form.

Figure 3:
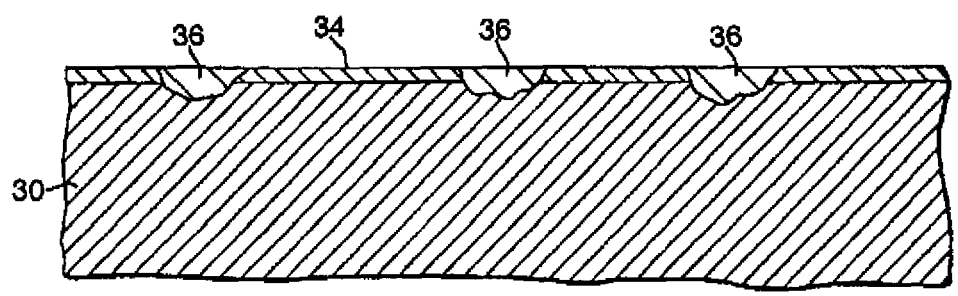
FIG. 3 shows a diagrammatic sectional view through part of the surface of a metal object in accordance with the invention.

As shown in FIG. 3, the metal object is used for an implant, but the same process may also be used to produce jewellery or it may also be used to produce medical devices or implements.

The implant 30 is first cleaned. The cleaning process may be by ultrasonic cleaning using first acetone as the liquid phase (or other degreasing solvent), then rinsed with fresh acetone (or other solvent) and followed by de-ionized water or any other suitable rinsing solution. The metal material may then be cleaned in a 1M aqueous solution of sodium hydroxide (or other alkaline cleaner) and then rinsed in de-ionized water. The resulting cleaned metal material is then anodised in contact with an aqueous solution of phosphoric acid. The concentration of the phosphoric acid is preferably in a range of from 0.5-5 M, more typically from 1 to 3 M, e.g. 2 M (or about 20 weight percent of solution). The implant is anodised using a voltage in the range from 15 to 150 V, more typically 50 to 150 V e.g. 100 V. The concentration of the anodising solution is 0.01 M to 5 M, typically 0.1 M to 3 M and in particular 2 M and the voltage used is 15-200 V, but typically it is in the range of 30 V to 150 V for example 35V. Such ranges may also apply to jewellery.

The voltage is preferably maintained until a desired growth of pits or pitted regions through the anodised surface layer into the substrate is attained. Preferably, the current density through the surface during anodising is monitored. A suitable current density limit during the initial film growth period is typically about 5 $mA/cm^2$, the voltage rising to a maximum constant value to produce a well anodised surface on the implant. The potential may be applied in a single step to its maximum value or it may be applied in steps, for example from 30V to 80V to 100V. Alternatively, the potential may be applied increasing linearly to its maximum value at a controlled rate of 0.1-10 V/s, preferably 0.5-5 V/s, ideally 1-2 V/s. The desired degree of anodising is usually obtained after a charge of from 2 to 5 coulombs/$cm^2$ of surface area of the implant has been passed. Preferably, the anodising process is carried out over a period of from 1 to 6 hours, e.g. from 2 to 4 hours. A suitable charge would be about 3.5 coulombs/$cm^2$.

The surface of the thus-anodised implant based on titanium comprises a hard layer 34 comprising a titanium oxide, and pits or pitted regions 36. The pits and/or pitted regions 36 are believed to contain titanium oxide and might also contain a soluble titanium compound. The pits typically have depths of up to 2 to 3 μm penetrating through the passive layer of 0.14 μm (at 100 V) into the substrate and have diameters of up to 5 μm. The pits may occupy some 5 to 20% of the surface area, though preferably below 10%. However, depending on the voltage applied and the length of time of treatment, there may be a range of depths and diameters for the pits, for example the depths may range from 1 to 5 μm, more typically 1 to 4 μm and the diameters may be anywhere between 0.1 to 20 more typically 1 to 10 μm, or 1 to 5 μm and these ranges can vary across the surface of the implant.

After the anodising step described above, a voltage is applied through the anodising solution in the reverse sense compared to the voltage (and therefore the current flow) during the anodising step. That is to say, the implant is given a negative polarity. During treatment with (e.g.) a 2.0 M aqueous phosphoric acid solution, the "reverse-sense" voltage (i.e. reversed relative to voltage (and current flow) during the anodising step) is applied with a voltage in the range of from −0.2 to −0.7 V, e.g. −0.3 to −0.6 V, more specifically −0.40 to −0.55 V, and exemplified by about −0.45 V (as measured with respect to a Ag/AgCl standard reference electrode), to ensure that the solvent, water, is not electrolysed, but that a reduction process is able to take place. It is believed that during the period of reversed voltage, certain titanium species are electrochemically reduced within the pits to high surface area, low solubility, hydrous titanium oxide species. The latter have a relatively low solubility at the electrolyte pH within the range 0.5-2, and it is believed that, as a result, the pits formed in the substrate metal through the anodised surface layer fill with this high surface area inorganic medium. As the reversed voltage is applied, the current through the implant drops from an initially high value, and eventually falls to zero or substantially zero. It is believed that the fall in current is due to the depletion of the reducible titanium species which results in the formation of the low-solubility hydrous titania species in the pits. Substantially complete reduction to the hydrous titania is typically attained after a cathodic charge in the range of from 0.005 to 0.2 coulomb/cm$^2$, e.g. in the range of from 0.01 to 0.05 coulomb/cm$^2$. When the reversed current has fallen sufficiently, e.g. to less than 60% and desirably to less than 20% of the peak value, preferably to zero or thereabouts, the reversed potential is stopped. The fall in the reversed current part of the procedure may take from 60 to 180 s. The overall anodising process is satisfactorily effected in a time period in the range 1 to 5 hours, e.g. from 2 to 4 hours, typically 2.5 to 3.5 hours, e.g. 3.0 hours or thereabouts.

It is also possible for this potential reversal stage to take place in a solution of anodization electrolyte containing dissolved peroxytitanyl salts synthesised chemically (e.g by dissolving Ti(OH)$_4$ in an acidic electrolyte solution containing hydrogen peroxide). (An equivalent process can be carried out using an alkaline electrolyte). No reduction reaction will take place at the passivated outer surface of the anodized item due to the semiconductor properties of this film, although the electroactive pits engineered through this film are able to permit the electroreduction process locally within the pit. For metal substrates—especially those non-titanium based materials e.g. Nb, Ta, Zr and their alloys—this may be a useful method of introducing the hydrous titania adsorber medium into the surface, prior to subsequent biocide adsorption. The adsorber can be based on the metal from which the implant is to be made, for example, zirconium, but for cost effectiveness, titania is used as a preference.

The anodising process forms a hard surface that can have different coloured appearances due to optical interference effects. During the initial steps of anodising, the surface colour varies from gold to purple, blue, through to colourless, green, yellow, orange and finally red/purple. Anodising at 100 V produces a film thickness of about 140 nm. Changing the voltage can alter the extent of anodising and hence the thickness of the hard surface, which in turn influences the colour formed. Different voltages alter the colour produced, for example in 2.0 M phosphoric acid, approximately 20 V, up to 35 V will produce a blue colour on the metal, e.g. an implant or jewellery. Having different coloured articles, not only provides different aesthetic effects but also allows for articles such as implants to be identified, for example, an implant for one purpose or from one manufacturer can be colour coded so that if it has to be removed or replaced, a medical practitioner can identify that implant as being of a certain type and they can then replace it with another implant of the same type. In the case of jewellery, different colours provide different degrees of attractiveness and this is particularly applicable to titanium based jewellery.

Once pores/pits are formed in the surface of the metal, surface engineering of the metal surface may also be employed to increase the loading of biocidal ions in the pits in the metal. Once the pits are formed, there may be surface engineering during step (b) where a subsequent increased voltage is applied to the metal or its alloy, for example 75V in the case of titanium, and this application of voltage results in breakdown of the surface in areas where there are defects in the surface or where there are local areas of small pits. The high voltage causes existing pits/defects in the surface to grow by widening in diameter and deepening due to the fact that the walls of the pits remain electroactive. Increasing the voltage again, for example greater than 35 V and up to 75 V results in some degree of passivation of the pit walls such that any subsequent electrolytic activity can be concentrated at the bottom of the pit, which prevents any ionic material that is deposited in the pit from protruding above the anodized surface.

When the anodising steps and reduction step have been completed (and any surface engineering process as discussed above), the surface of the anodised implant is rinsed with de-ionised water to remove phosphoric acid residues and other soluble materials. The thus-cleaned implant is next immersed in a solution comprising the biocidal material, which is silver in this example. The solution is an aqueous solution of silver nitrate having a silver concentration in the range of from 0.001 to 10 M, e.g. 0.01 to 1.0 M, for example, 0.1 M or thereabouts.

The treated implant may have a silver content of 0.5 to 40 µg/cm$^2$ or more typically from 2-20 µg/cm$^2$. The silver is present initially mainly in ionic form but may be at least partially converted to atomic clusters of metal dispersed within the hydrous titania adsorption matrix as a result of photo-reduction. Typically, ~0.3-1 µg/cm2 is adsorbed on the outer passive layer, with the remainder stored within the hydrous titania-filled pits.

Figure 4:
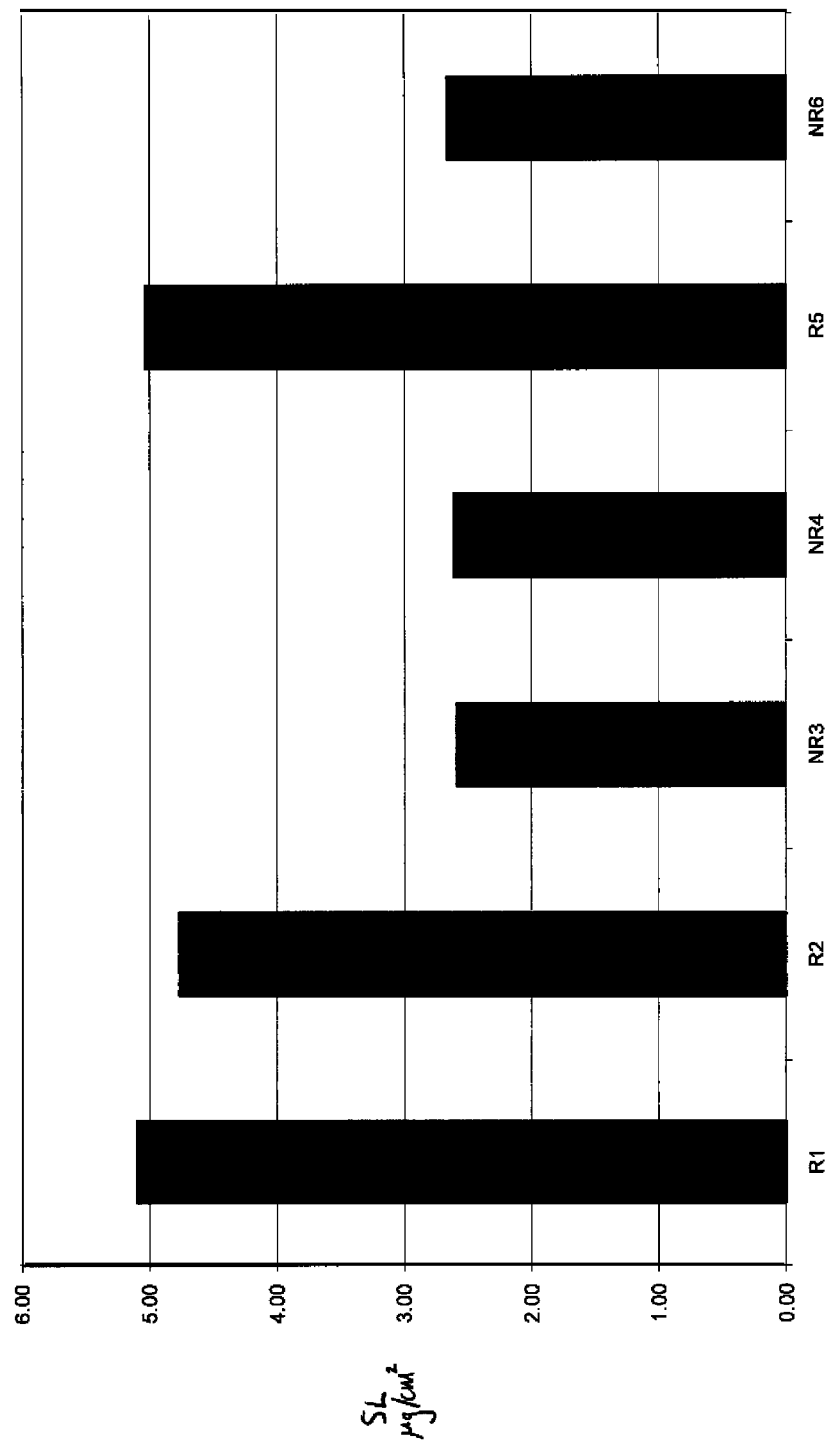
FIG. 4 shows a comparison of loading of silver in pits in three samples, with and without the use of a negative voltage.

FIG. 4 shows a graph for 6 samples where a reduced voltage is applied and these are shown as R1, R2 and R5. There are also three samples where no reduced voltage is applied NR3, NR4 and NR6.

Discs of titanium were anodized in 2.1M of $H_3PO_4$ to an initial voltage of 100V with a current limit of 5 mA/cm$^2$ at 20° C. The voltage was then reduced to −0.45V (levels of between −0.05V and −1.0V, more typically −0.1V and −0.60V can be used. This step was omitted for the "NR" samples. The silver loading process involved placing the metal in 0.1M silver nitrate for 1 hr. The silver loading (SL) is shown as µg/cm2 which relates to the geometric area. As can be seen, the loading of the pits where there is voltage reduction shows a significantly improved level of loading than when no voltage reduction is applied. The increase in loading may be up to a factor of two.

It is thought that during anodization, $TiO_2^{2+}$ is generated locally as the phosphate salt through titanium dissolution under the anodic conditions in the pits. On subsequent reversal, this will be reduced to $Ti(OH)_4$ (hydrous titania), which is essentially insoluble in the electrolyte above a pH of around 0.5, and so this material is retained in the pit/pore as a solid. The hydrous titania is an inorganic ion-exchange medium that can become saturated with cations such as silver cations when contacted with silver nitrate, $AgNO_3$, solution and this results in an increased level of silver. Hydrous titania is also known to be a catalyst for the photoreduction of silver cations to the metallic species, which may result in the conversion of some of the adsorbed ionic silver to dispersed metallic silver within the adsorber matrix.

It is thought that during exposure to body fluids, there is a slow leaching of silver species from the anodised layer, so that the growth of microorganisms such as bacteria, yeasts or fungi in the vicinity of the metal object is inhibited. The leaching is thought to be effected by ion exchange of silver on the metal object with sodium in the body fluids that contact the metal object. Other mechanisms such as the oxidation of the metallic silver to ionic species by means of the localised oxygen levels can occur to produce the released silver ions which can go on to kill or suppress the growth of the microorganisms or the biofilm formation.

The method of the invention described hereinabove may be employed for the preparation of a range of metal objects which involve the treatment with an anodising electrolyte. In particular, the invention has applications to metal articles that are formed of titanium or which are titanium alloys, and those of zirconium, niobium, tantalum or their alloys.

The silver incorporated in the surface by the method of the invention is at a more consistent concentration than previously attained by known methods and hence the biocidal properties of the novel implants according to the invention are enhanced compared to previous implants. For example, for nine sample implants prepared under identical conditions according to the present invention, a mean silver loading of 9.8 µg Ag/cm$^2$ was obtained. The ratio of standard deviation of values to this mean was only 6%, demonstrating a very narrow spread of silver loading attained by the method of this invention. This high consistency of biocidal metal loading is highly desirable for implants. The method according to the present invention imparts a considerable improvement in the consistency of silver loading and a higher silver loading over known methods.

It is to be understood that references herein to silver as a biocidal metal also apply to other biocidal metals, such as copper, gold, platinum, palladium or mixtures thereof, either alone or in combination with other biocidal metal(s).

It is also envisaged that a bone promoting material may be coated on the metal implant once the biocidal material has been introduced such as hydroxyapatite.

Although individual embodiments of the invention are discussed, it is to be understood that combinations of the individual embodiments fall within the scope of the invention as claimed and described.

The invention claimed is:

1. A method treating a metal object so as to form thereon a surface layer which is integral with the metal object, and which includes a biocidal material, the method comprising:
   (a) immersing the metal object, which is to provide a substrate for the surface layer, in an anodising electrolyte containing a solvent, and anodising the metal object to passivate it by forming an anodised integral surface layer on the metal object by applying a positive voltage between 15 and 200 V;
   (b) continuing the anodising of the metal object by the application of a positive voltage, to produce pits through the integral surface layer and into the substrate;
   (c) then, after anodising the metal object during steps (a) and (b), producing a hydrous metal oxide or phosphate by:
   (i) applying a negative voltage which is insufficient to cause electrolysis of the solvent to the metal object, while in contact with the anodising electrolyte, or
   (ii) contacting the metal object with an electrolyte solution containing a reducible soluble salt of titanium or the substrate metal and an other solvent and applying a negative voltage which is insufficient to cause electrolysis of the other solvent;
   (d) removing or separating the anodised metal object resulting from step (c) from the anodising electrolyte or the electrolyte solution; and
   (e) then contacting the anodised metal object with a solution containing a biocidal material so as to incorporate said biocidal material into the surface layer.

2. The method of claim 1, wherein the voltage applied in step (b) is a different voltage to that applied during the passivation of step (a).

3. The method of claim 1, wherein step (c)(ii) is performed, and the electrolyte solution of step (c)(ii) contains a peroxy cationic complex of a metal of Groups IVa, Va and VIa of the Periodic Table.

4. The method of claim 1, wherein the biocidal material comprises a biocidal metal.

5. The method of claim 4, wherein the biocidal metal comprises silver.

6. The method of claim 1, wherein the metal of the metal object comprises titanium, niobium, tantalum, zirconium and/or an alloy thereof.

7. The method of claim 1, wherein the anodising electrolyte is phosphoric acid at a concentration in the range of 1.0 to 3.0 molar.

8. The method of claim 7, wherein step (c)(i) is performed, and the negative voltage has a magnitude in a range of from −0.2 to −0.7 volt with respect to a Ag/AgCl reference electrode, and wherein the electrolyte has a phosphoric acid concentration of substantially 2.0 molar.

9. The method of claim 1, wherein step (c)(i) or step (c)(ii) comprises applying the negative voltage to the metal object at least until the current through the object falls to a value no higher than 20% of its initial value.

10. The method of claim 1, wherein the anodised metal object is treated with a solvent to remove electrolyte and soluble cations prior to contacting it with the solution containing the biocidal material.

11. The method of claim 1, wherein the anodising is performed with a current density in a range of from 0.1 to 25 mA/cm$^2$.

12. The method of claim 1, wherein the anodising is performed at a voltage increasing at a rate in the range 0.1-10 V per second.

13. The method of claim 1, wherein the amount of charge employed for anodising is in the range from 1 to 10 coulomb/cm$^2$.

14. The method of claim 1, wherein the anodising is performed in the presence of an electrolyte, and movement and circulation of the electrolyte relative to the surface of the metal object is inhibited or suppressed, at least during the pit growth phase of step (b).

* * * * *